(12) United States Patent
Gomez, Jr. et al.

(10) Patent No.: US 8,449,486 B2
(45) Date of Patent: May 28, 2013

(54) BACK AND NECK CUSHION THERAPY DEVICE

(76) Inventors: Jose Gomez, Jr., Humble, TX (US); Victor B. Ramos, Houston, TX (US)

( * ) Notice: Subject to any disclaimer, the term of this patent is extended or adjusted under 35 U.S.C. 154(b) by 148 days.

(21) Appl. No.: 12/839,293

(22) Filed: Jul. 19, 2010

(65) Prior Publication Data

US 2011/0118644 A1    May 19, 2011

Related U.S. Application Data

(63) Continuation-in-part of application No. 12/619,230, filed on Nov. 16, 2009, now Pat. No. 8,414,514, and a continuation-in-part of application No. 12/619,261, filed on Nov. 16, 2009, now abandoned, and a continuation-in-part of application No. 12/619,279, filed on Nov. 16, 2009.

(51) Int. Cl.
| | |
|---|---|
| *A61F 5/00* | (2006.01) |
| *A47C 3/00* | (2006.01) |
| *A61G 15/00* | (2006.01) |
| *A61H 7/00* | (2006.01) |
| *A41D 13/00* | (2006.01) |

(52) U.S. Cl.
USPC ....... 602/36; 297/284.1; 128/845; 128/106.1; 601/134; 2/463; 2/464; 2/467; 5/632; 5/633

(58) Field of Classification Search
USPC ........ 602/32, 36, 37; 601/134–138, 143–147, 601/124, 128, 131–32, 56; 5/632–633, 640, 5/657; 482/91; 297/284.1–284.11, 219.12, 297/397; 2/463–464, 467
See application file for complete search history.

(56) References Cited

U.S. PATENT DOCUMENTS

| | | | | | |
|---|---|---|---|---|---|
| 395,043 | A | * | 12/1888 | Doremus | 5/640 |
| 2,765,480 | A | * | 10/1956 | Mueller | 5/640 |
| 4,876,755 | A | * | 10/1989 | Parrish | 297/284.3 |
| 5,503,456 | A | * | 4/1996 | Rossini | 297/397 |
| 6,182,311 | B1 | * | 2/2001 | Buchanan et al. | 5/632 |
| 7,207,630 | B1 | * | 4/2007 | Reynolds | 297/397 |
| 7,378,975 | B1 | * | 5/2008 | Smith et al. | 340/573.1 |
| 7,703,849 | B2 | * | 4/2010 | Bilak et al. | 297/284.6 |
| 2008/0066233 | A1 | | 3/2008 | Russell | |

* cited by examiner

*Primary Examiner* — Patricia Bianco
*Assistant Examiner* — Tarla Patel
(74) *Attorney, Agent, or Firm* — Buskop Law Group, PC; Wendy Buskop (57) ABSTRACT

A back and neck cushion therapy device for wearing, attaching to a backpack, or placing over a chair. The device can include a pouch with a traction device disposed therein. The traction device can include a head, a body, and a lower back traction. Straps can be connected to the pouch, allowing a user to strap the device about the user. The traction device can have various indention load deflections, providing firmness or softness. The traction device can be shearable, allowing the user to cut the traction device to a custom size. The pouch can be fastened to a backpack. A reversible back and neck cushion therapy device can include two pouches with two traction devices, such that a user can select a firm side or a soft side. The reversible back and neck cushion therapy device can be hung over a chair back.

6 Claims, 7 Drawing Sheets

BACK AND NECK CUSHION THERAPY DEVICE

CROSS REFERENCE TO RELATED APPLICATIONS

The present application is a continuation-in-part of: co-pending U.S. patent application Ser. No. 12/619,230 filed on Nov. 16, 2009, entitled "WEARABLE AMBULATORY TRACTION SYSTEM"; co-pending U.S. patent application Ser. No. 12/619,261 filed on Nov. 16, 2009, entitled "REMOVABLE CHAIR SUPPORTED TRACTION SYSTEM"; and co-pending U.S. patent application Ser. No. 12/619,279 filed on Nov. 16, 2009, entitled "METHOD FOR TREATING A USER'S BACK OR NECK USING A TRACTION SYSTEM". These references are incorporated herein in their entirety.

FIELD

The present embodiments generally relate to a back and neck cushion device for providing therapeutic relief to a user's back, neck, or combinations thereof.

BACKGROUND

A need exists for a cushion therapy device that provides therapeutic relief to a user's back, neck, or combinations thereof.

A need exists for a cushion therapy device that can be attached to a harness, a chair, or a backpack for transportable use.

A need exists for a reversible cushion therapy device that can provide user's with both firm support and soft support depending upon the user's needs.

A further need exists for a cushion therapy device that is customizable for use by any user.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a back and neck cushion therapy device for providing therapeutic relief to a user's back, neck, or combinations thereof.

The device can provide user's with an economical alternative to costly professional physical therapy or surgery by providing therapeutic stress relief and relaxation to users experiencing muscular or skeletal pains, tensions, or other muscular or skeletal ailments. For example, embodiments can be used to decompress stress in a user's back, neck, or combinations thereof, thereby providing the user with greater flexibility, relieving muscular tension, and leading to faster recovery from muscle cramps, aches, and pains. Also, embodiments can be used to remind a user to maintain proper posture.

The back and neck cushion therapy device can include a traction device which can be a cushion. The traction device can include a traction head, a traction body, a lower back traction and one or more centralizers. The traction head, traction body and lower back traction can be substantially tubular, any shape, or any form. The traction head can engage with the traction body at an angle, such as a right angle. The traction body can engage with the lower back traction at an angle, such as a right angle.

During use of the back and neck cushion therapy device, a user can place the traction head behind or proximate the user's neck. The user can place the traction body behind or proximate the user's spine. The user can place the lower back traction behind or proximate the user's lower back. The traction device can thereby provide a therapeutic cushioning to the user's back and neck.

In one or more embodiments, an adhesive can provide engagement between the traction head and the traction body, and between the traction body and the lower back traction.

The traction head, traction body and lower back traction can each be cylindrically shaped or another shape. The traction head, traction body and lower back traction can have identical diameters or different diameters. The lower back traction can be longer or shorter than the traction head.

Each traction device can be formed of a foam, closed cell foam, polypropylene, polyethylene, polyurethane, an extruded foam polymer, a sponge like material, a memory foam such as a visco-elastic polyurethane memory foam, or another foam polymer.

In one or more embodiments, the traction head can have a first hole disposed along an axis of the traction head. The first hole can be a through hole. The traction head can have a second hole disposed through the traction head perpendicular to the first hole. The second hole can be in communication with the first hole. A support member can be disposed within the traction head, such as within the first hole and the second hole. A centralizer can be engaged with the support member. The support member can have a left tube axially aligned with the traction head and disposed within a left portion of the first hole of the traction head. The support member can have a right tube axially aligned with the traction head and disposed within a right portion of the first hole of the traction head. The left tube can be connected to the right tube. The support member can have a central tube disposed transverse to the left and right tubes, and disposed within the second hole of the traction head. The central tube can be centrally connected to the left tube and the right tube. The left tube, the right tube, and the central tube can be a one-piece integral structure. The central tube can engage the centralizer. The centralizer can extend from the traction head, out of the second hole of the traction head, and can engage the traction body. For example, the traction body can have a hole disposed at a top of the traction body. The centralizer of the traction head can engage into the hole of the traction body. The support member can provide a sturdy engagement between the traction head and the traction body and/or between the traction body and the lower back traction. The centralizer can centrally engage the traction body. In embodiments, the centralizer can be formed as a substantially tubular member and can be hollow or solid.

In one or more embodiments, the lower back traction can have a first hole disposed along an axis of the lower back traction. The first hole can be a through hole. The lower back traction can have a second hole disposed through the lower back traction perpendicular to the first hole. The second hole can be in communication with the first hole. A support member can be disposed within the lower back traction, such as within the first hole and the second hole. A centralizer can be engaged with the support member. The centralizer can the support member can be formed substantially as described above with respect to the traction head. The centralizer can centrally engage the traction body. The traction head can be engaged with the traction body at a right angle. The lower back traction can be engaged with the traction body at a right angle. The lower back traction can be disposed parallel to the traction head.

In embodiments, the centralizer can be a flexible centralizer that can extend from the traction head and/or the lower back traction, and can engage the traction body, providing a flexing engagement. The centralizer can be removable from the support member and can be elastic.

The traction device can have a coating disposed thereon. The coating can be a water-proof or a water-resistant coating that can resist the penetration of sweat from a user's body.

In embodiments, a heating element or a cooling element can be disposed within at least a portion of the traction device, allowing a user to adjust a temperature of the traction device.

The back and neck cushion therapy device can include a fabric garment which can have a front portion for covering a front portion of a user's body, and a back portion for covering a back portion of the user's body. The fabric garment can be a wearable fabric garment. In embodiments, the fabric garment can be disposed over a chair.

The chair can be an airplane seat, an automobile seat, a truck seat, a folding stadium seat, an office chair, a movie theater seat, an auditorium seat, a folding chair, a lawn chair, a dining room chair, a motor cycle high-back chair seat, a tractor chair, a vehicle seat, another seat, any type of chair, any type of seat, or a similar device.

The fabric garment can be any number of fabric garments including but not limited to a sheath, a shirt, a T-shirt, a long sleeved shirt, a vest, a cardigan, a hoodie, a jacket, a poncho, a coat, a sweater, a backpack, a v-neck shirt, or a robe.

The back and neck cushion therapy device can include a pouch. The pouch can be secured to the fabric garment, such as to the back portion of the fabric garment. The traction device can be insertable into an opening of the pouch. The traction device can be at least partially disposed within the pouch, or fully disposed within the pouch. The pouch can contain the traction device in a removable engagement, or the traction device can be non-removably enclosed within the pouch. In embodiments, the pouch can be a closable pouch. The pouch can be rectangular in shape, or another shape, and can have dimensions of about eleven inches by about twenty two inches, or other dimensions.

In embodiments, the pouch can be sewn onto the fabric garment. The pouch can also be removably attached to the fabric garment, such as by using a hook and loop fastener or another type of removable attachment. The pouch can be secured to an inside surface of the fabric garment and the traction device can be insertably engaged within the pouch.

In embodiments, the fabric garment can be worn by a user. A user can apply a pressure to the traction device using the user's back while the traction device is engaged with a surface, thereby allowing the traction device to provide a therapeutic pressure to the user's back, to the user's neck, or combinations thereof. The surface can be the surface of a bed, the back of a chair, the floor, or another surface.

One or more embodiments relate to a harness with a back and neck cushion therapy device, wherein the pouch is attached to the harness instead of to a fabric garment. The harness and/or pouch can include at least one adjustable webbing strap connected thereto, allowing a user to strap the back and neck cushion therapy device about the user such that the traction device is disposed proximate the user's back, neck, or combinations thereof.

The at least one adjustable webbing strap can include a first adjustable lower webbing strap connected to the pouch and a second adjustable lower webbing strap connected to the pouch. The first adjustable lower webbing strap can be engageable with the second adjustable lower webbing strap. For example, the first adjustable lower webbing strap can connect to the second adjustable lower webbing strap with a strap fastener. The second adjustable lower webbing strap can have a strap fastener, or a first adjustable fastener, that can be configured to engage the first adjustable lower webbing strap.

The at least one adjustable webbing strap can include a first adjustable upper webbing strap connected to the first adjustable lower webbing strap, and a second adjustable upper webbing strap connected to the second adjustable lower webbing strap. The first adjustable upper webbing strap can be engageable with the second adjustable upper webbing strap. The first adjustable lower webbing strap can connect to the first adjustable upper webbing strap with a strap fastener, the second adjustable lower webbing strap can connect to the second adjustable upper webbing strap with a strap fastener, and the first adjustable upper webbing strap can connect to the second adjustable upper webbing strap with a strap fastener. The second adjustable upper webbing strap can have a strap fastener, or a second adjustable fastener, that can be configured to engage the first adjustable upper webbing strap.

The at least one adjustable webbing strap can include a first adjustable shoulder webbing strap connected to the pouch and to the first adjustable upper webbing strap, and a second adjustable shoulder webbing strap connected to the pouch and to the second adjustable upper webbing strap. A first shoulder pad can be connected to the first adjustable shoulder webbing strap, and a second shoulder pad connected to the second adjustable shoulder webbing strap.

Each strap fastener can be an adjustable buckle, an adjustable parachute buckle, or another adjustable fastener, such that the user can tighten or loosen the webbing straps to fit the user. Each webbing strap can be made of nylon webbing, a seatbelt material, or another strap material.

A user can wear the harness with the back and neck cushion therapy device anywhere that the user goes, providing the user with a mobile cushion. A user wearing the harness with the back and neck cushion therapy device can sit or stand against a surface, such as the back of a chair, a floor, or a bed to receive a therapeutic cushioning experience.

In one or more embodiments of the back and neck cushion therapy device, the traction device can be disposed within a fabric portion. The fabric portion can be sewed about a surface of the traction device. The fabric portion can be sewed directly over the surface of the traction device and can be flush with the surface of the traction device, thereby allowing the back and neck cushion therapy device to fit between shoulder straps of a backpack. The fabric portion can be attached to a backpack or a frame of a backpack. The fabric portion can include at least one strap connected thereto. The at least one strap, or at least one webbing strap, can be configured to be fastened to the backpack or the backpack frame. For example, the at least one strap can be fastened to the backpack, such that when a user wears the backpack, the traction device within the fabric portion can be disposed between the backpack and the user's back, neck, or combinations thereof, providing a therapeutic cushioning of the weight of the backpack on the user's back and/or neck. The at least one strap can be a webbing strap as described herein. During use, the lower back traction can absorb the weight of the backpack, and can evenly distribute that weight, thereby simultaneously protecting a user's lower back, upper back, neck, kidneys, and body parts associated with the back and neck region from the pressures exerted by the backpack.

One or more embodiments relate to a back and neck cushion therapy device including two pouches attached to each other, providing a reversible back and neck cushion therapy device.

The reversible back and neck cushion therapy device can include a first pouch with at least one side strap. A first traction device can be at least partially disposed inside the first pouch. The reversible back and neck cushion therapy device can include a second pouch with at least one side strap. A second traction device can be at least partially disposed inside the second pouch. The second traction device can have a lower indention load deflection than the first traction device, thereby providing a reversible back and neck cushion therapy device having a soft cushion traction device and a firm cushion traction device. During use, if a user wants a firm cushion, the user can dispose the reversible back and neck cushion therapy device such that the firm cushion traction device is disposed directly behind the user's back, neck, or combinations thereof. If the user then wants to change to a soft cushion, the user can dispose the reversible back and neck cushion therapy device such that the soft cushion traction device is disposed directly behind the user's back, neck, or combinations thereof.

The reversible back and neck cushion therapy device can include at least one connecting strap connecting between the first pouch and the second pouch, allowing the user to hang the first pouch and the second pouch over a chair, a bed, or a substantially rigid surface. For example, the user can dispose the reversible back and neck cushion therapy device over the chair such that either the first pouch or the second pouch is disposed between the user and the chair.

The at least one side strap of the first pouch can be engageable with the at least one side strap of the second pouch, allowing the user to strap the reversible back and neck cushion therapy device to the chair, the bed, or another substantially rigid surface. For example, after the user disposes the reversible back and neck cushion therapy device over the back of the chair, the user can attach the at least one side strap of the first pouch and the at least one side strap of the second pouch together using a fastener, such as a hook and loop fastener.

The combination of the reversibility and the two different indention load deflections allows a user to simultaneously have a softer back and neck cushion therapy device and a firmer back and neck cushion therapy device at the user's disposal.

The reversible back and neck cushion therapy device can be disposed over a flat rigid surface, such as a floor, allowing the user to receive back and neck stimulation from either the first traction device or the second traction device.

In one or more embodiments, each strap of the reversible back and neck cushion therapy device can be an elastic strap. The first pouch can include a first side strap and a second side strap. The second pouch can also include a first side strap and a second side strap. The first side strap of the first pouch can be fastened to the first side strap of the second pouch with a fastener, such as a hook and loop fastener. The second side strap of the first pouch can be fastened to the second side strap of the second pouch, such as with a hook and loop fastener.

Embodiments of the back and neck cushion therapy device can be ambulatory. A user can move and walk about while wearing the pouch with the traction device, such as the pouch with the harness or the pouch on the backpack. A user can therefore go from using the back and neck cushion therapy device at home, to using the back and neck cushion therapy device at work, and then to using the back and neck cushion therapy device at another location; all while continuously wearing the pouch with the traction device.

A user can interchange different traction devices within each pouch. For example, a user can a have a soft traction device that the user can use with a harness and pouch. When the user wants a more firm traction device, the user can remove the soft traction device and insert the firm traction device into the pouch.

The pressure applied by the user's back and/or neck can be applied for a predetermined time interval. A predetermined time interval can be an amount of time a user determines to apply the pressure. The predetermined time interval can be variable and can be any amount of time chosen by the user.

The pressure applied by the user's back can be a variable user-specified pressure. The user can vary the pressure using a weight of at least a portion of the user's body that is in engagement with the traction device. A user can vary the pressure by applying more or less pressure to the traction device using the user's back. A user can apply the pressure in a series of pressure cycles to provide a decompressive therapeutic pressure to the user's back, neck, or combinations thereof.

The engagement between the traction head and the traction body, as well as between the traction body and the lower back traction, can be at a variable angle. In embodiments, the variable angle can range from about 83 degrees to about 97 degrees. The variable angle can allow a user to adjust the angle of the engagement to accommodate a position of the user's neck and/or back. For example, during use, if a user leans or bends the user's neck, the variable angle can allow the traction head to bend along with the user's neck, providing support and therapy to the user's neck even when the user's neck is bent. A flexible centralizer can allow the traction head and lower back traction to bend along the variable angle with respect to the traction body.

In embodiments, the pouch can include a message portion. The message can be an advertisement, a slogan, a logo, a sports logo, an instruction explaining how to use the device, an identification of the product, a telephone number, a website address, a personal message, a photo, or another message.

Embodiments can include a pressure sensor disposed within or on the traction device. The pressure sensor can be in electrical communication with an alarm which can also be disposed within or on the traction device. A preset pressure limit can be a maximum pressure that a user determines should be applied to the traction device by the user's back and/or neck. The pressure sensor can measure the pressure applied by a user's back and/or neck, and when the pressure applied by the user's back and/or neck exceeds the preset pressure limit, the pressure sensor can send an electronic signal to the alarm to provide an alert to the user. The alert can be an audio signal, such as a sound from a speaker; a visual signal, such as a blinking light; or both.

Embodiments can include a time sensor which can be actuated to begin measuring time when a user applies pressure to the traction device. When the user ceases to apply pressure to the traction device, the time sensor can stop measuring time. A preset time limit can be a maximum time that a user determines pressure should be applied to the traction device by the user's back and/or neck. The time sensor can measure the usage time in which pressure is applied by a user's back and/or neck. When the usage time exceeds the preset time limit, the time sensor can send an electronic signal to the alarm to provide an alert to the user. The time sensor can be in electrical communication with the alarm, the pressure sensor, or both.

The alarm can provide the alert to the user when the pressure applied by the user's back is greater than a preset pressure limit, when a usage time is greater than a preset time limit, or combinations thereof.

In embodiments, the pressure sensor, the time sensor, and the alarm can be in electrical communication with a processor which can be in electrical communication with a data storage. The preset pressure limit and the preset time limit can be stored on the data storage and can be reprogrammed or adjusted to accommodate various different users.

The data storage can have computer instructions stored thereon. The computer instructions can include: computer instructions to compare a measured pressure applied by a user's back and/or neck to the preset pressure limit; computer instructions to compare a measured time to the preset time limit; computer instructions to provide an alarm; or combinations thereof.

In embodiments, the traction device can have a vibration member disposed on it that can produce vibrations for relaxing the user. A power source can be in electrical communication with the vibration member, time sensor, pressure sensor, alarm, processor, data storage, or combinations thereof.

In embodiments, the back and neck cushion therapy device can be customizable. The traction head, traction body, and lower back traction can each be shearable, allowing a user to cut the traction device to a custom size. Users of various ages can have various sizes, shapes, and heights. The customizable traction device allows a user to customize a size of the traction device such that it fits the user's body, thereby allowing a wide variety of users to use the traction device.

The shearable traction device can have a plurality of dimensional indicators disposed thereon. The dimensional indicators can provide the user with indications of where to shear or cut the traction device such that the traction device is custom sized to fit the particular user. For example, the traction body can be sheared or cut to fit a length of a particular user's spine.

In embodiments, the traction head, traction body and lower back traction can each have an indention load deflection ranging from about ten (10) pounds to about eighty (80) pounds; however the traction head, traction body and lower back traction can have other indention load deflections. A twenty five (25) percent indention load deflection measurement of a traction head, traction body or lower back traction can be measured by indenting or compressing the traction head, traction body or lower back traction by twenty five (25) percent of its original dimensional magnitude. The amount of force, in pounds, required to indent the traction head, traction body or lower back traction by twenty five (25) percent of its original dimensional magnitude is equal to the twenty five (25) percent indention load deflection. A greater force required to compress the traction head, traction body or lower back traction, corresponds to a firmer traction head, traction body or lower back traction.

The traction head, traction body, and lower back traction can each have a different indention load deflection or the same indention load deflection. For example, a user might require a softer traction body and lower back traction for placement behind the user's back, and a firmer traction head for placement behind the user's neck. For such uses, the traction device can have a traction head with a higher indention load deflection, such as forty (40) pounds, and a traction body and lower back traction with a lower indention load deflection, such as eighteen (18) pounds. Alternatively, the user can have a traction body and lower back traction with a higher indention load deflection, such as forty (40) pounds, and a traction head with a lower indention load deflection, such as eighteen (18) pounds.

Embodiments of the traction device can have a density of one and one half (1.5) pounds per cubic foot. However, the traction device can have other densities as well.

The traction device can be customizable, wherein various sizes of traction heads with various indention load deflections can be interchangeable, and can be used with various sizes of interchangeable traction bodies and lower back tractions with various indention load deflections.

The traction body can have a length that can vary from about twelve (12) inches to about thirty (30) inches; however the traction body can be other lengths. The traction head can have a length that can vary from about five (5) inches to about seven (7) inches; however the traction head can be other lengths. The traction head and body can each have a diameter that can vary from about two (2) inches to about five (5) inches. Each centralizer can have a length configured to provide a stable engagement between the traction head and the traction body, and the traction body and the lower back traction. In one or more embodiments, the centralizer can have a length ranging from about four (4) inches to about ten (10) inches; however the centralizer can be other lengths as well.

Figure 1:
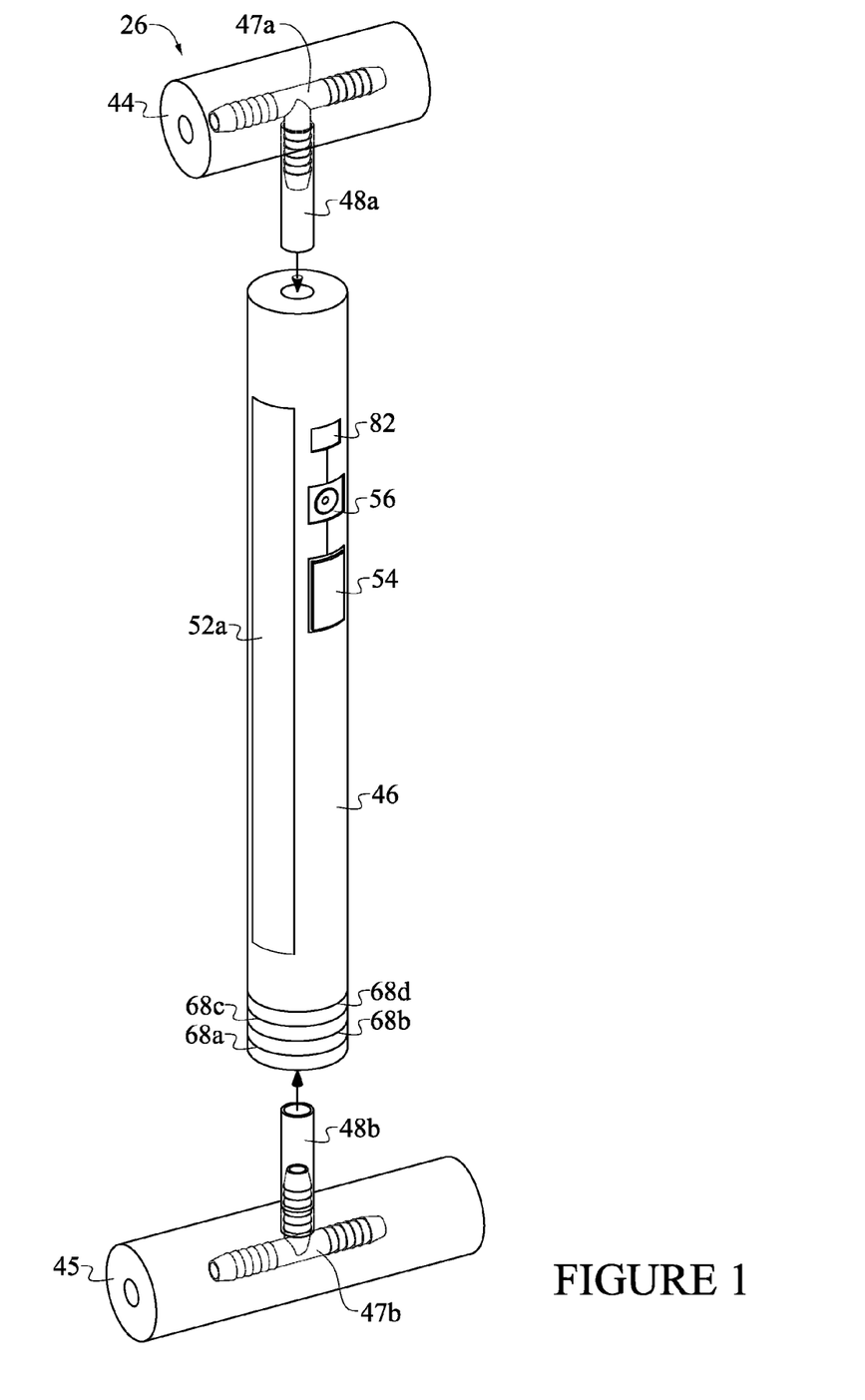
FIG. 1 shows an embodiment of a traction device.

Turning now to the figures, FIG. 1 shows an embodiment of a traction device 26. The traction device 26 can have a traction head 44, a traction body 46, and a lower back traction 45.

An upper centralizer 48a can extend from the traction head 44 and engage the traction body 46. The upper centralizer 48a can also engage with an upper support member 47a. The upper support member 47a can be disposed within the traction head 44.

A lower centralizer 48b can extend from the lower back traction 45 and engage the traction body 46. The lower centralizer 48b can also engage with a lower support member 47b. The lower support member 47b can be disposed within the lower back traction 45.

A pressure sensor 54 and a time sensor 82 can be disposed on the traction body 46, and can both be in electrical communication with an alarm 56. Also shown is a message portion 52a that can be disposed on the traction body 46. The traction body 46 can be a shearable traction body, and can have a plurality of dimensional indicators 68a, 68b, 68c, and 68d.

Figure 2:
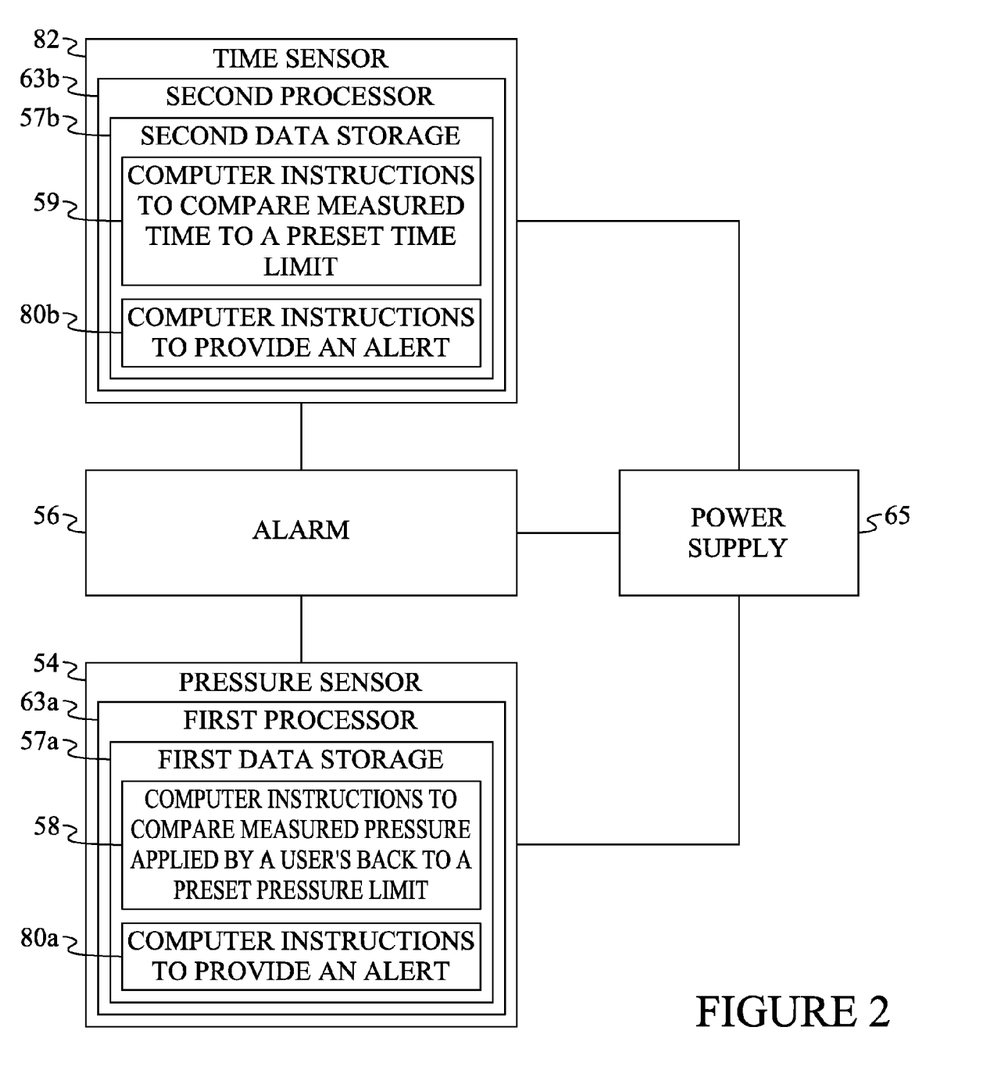
FIG. 2 shows an embodiment of a pressure sensor, a time sensor, an alarm, and a power supply.

FIG. 2 shows an embodiment of the pressure sensor 54, the time sensor 82, and the alarm 56, each in electrical communication with a power supply 65. The pressure sensor 54 and the time sensor 82 can each be in electrical communication with the alarm 56. The power supply 65 can be a battery or another source of electrical power.

The pressure sensor 54 can have a first processor 63a and a first data storage 57a. Computer instructions can be stored in the first data storage 57a including: computer instructions to compare measured pressure applied by a user's back to a preset pressure limit 58, and computer instructions to provide an alert 80*a* when the pressure is greater than a preset limit.

The time sensor 82 can have a second processor 63*b* and a second data storage 57*b*. Computer instructions can be stored in the second data storage 57*b* including; computer instructions to compare measured time to a preset time limit 59, and computer instructions to provide an alert 80*b* when a usage time is greater than a preset limit.

Figure 3:
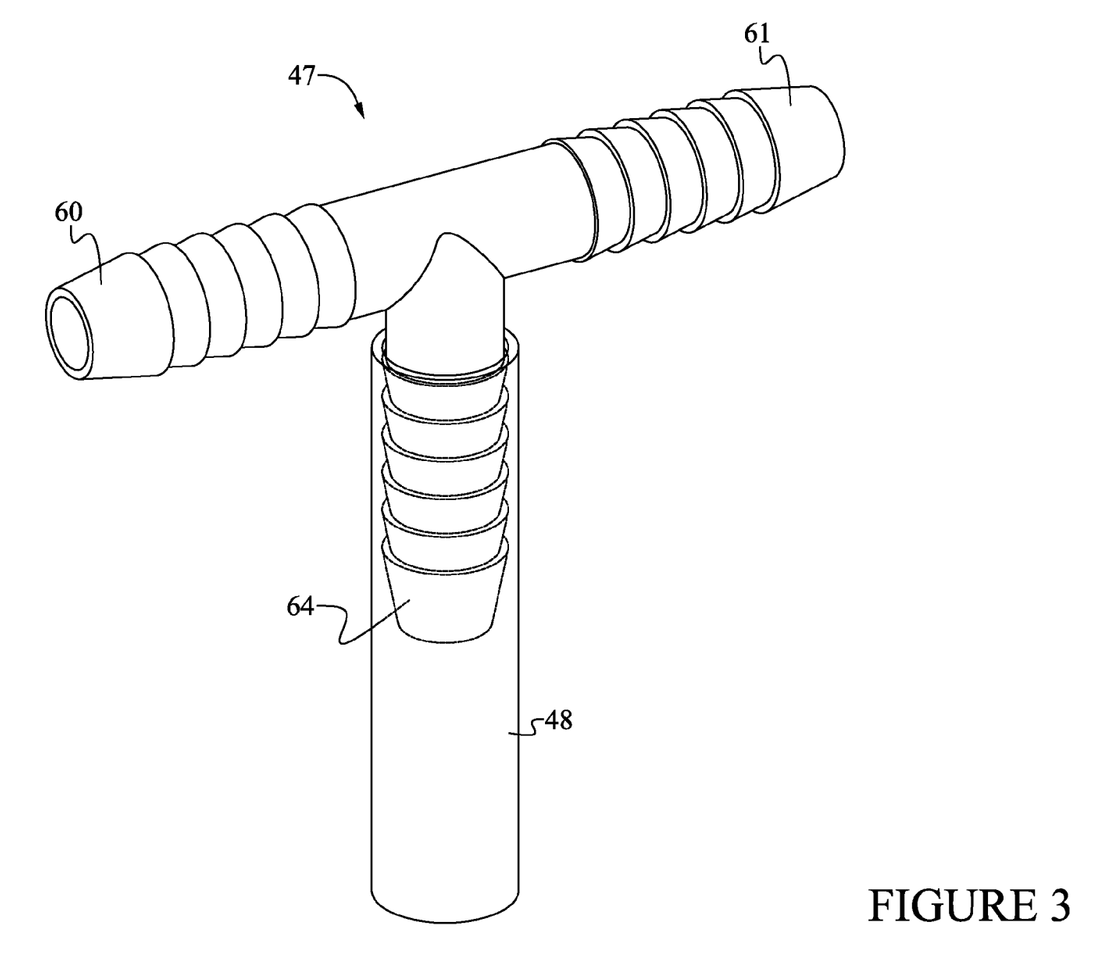
FIG. 3 shows a support member of a traction head.

FIG. 3 shows an embodiment of a support member 47 having a left tube 60, a right tube 61, and a central tube 64. A centralizer 48 is shown disposed on and engaged with the central tube 64.

Figure 4:
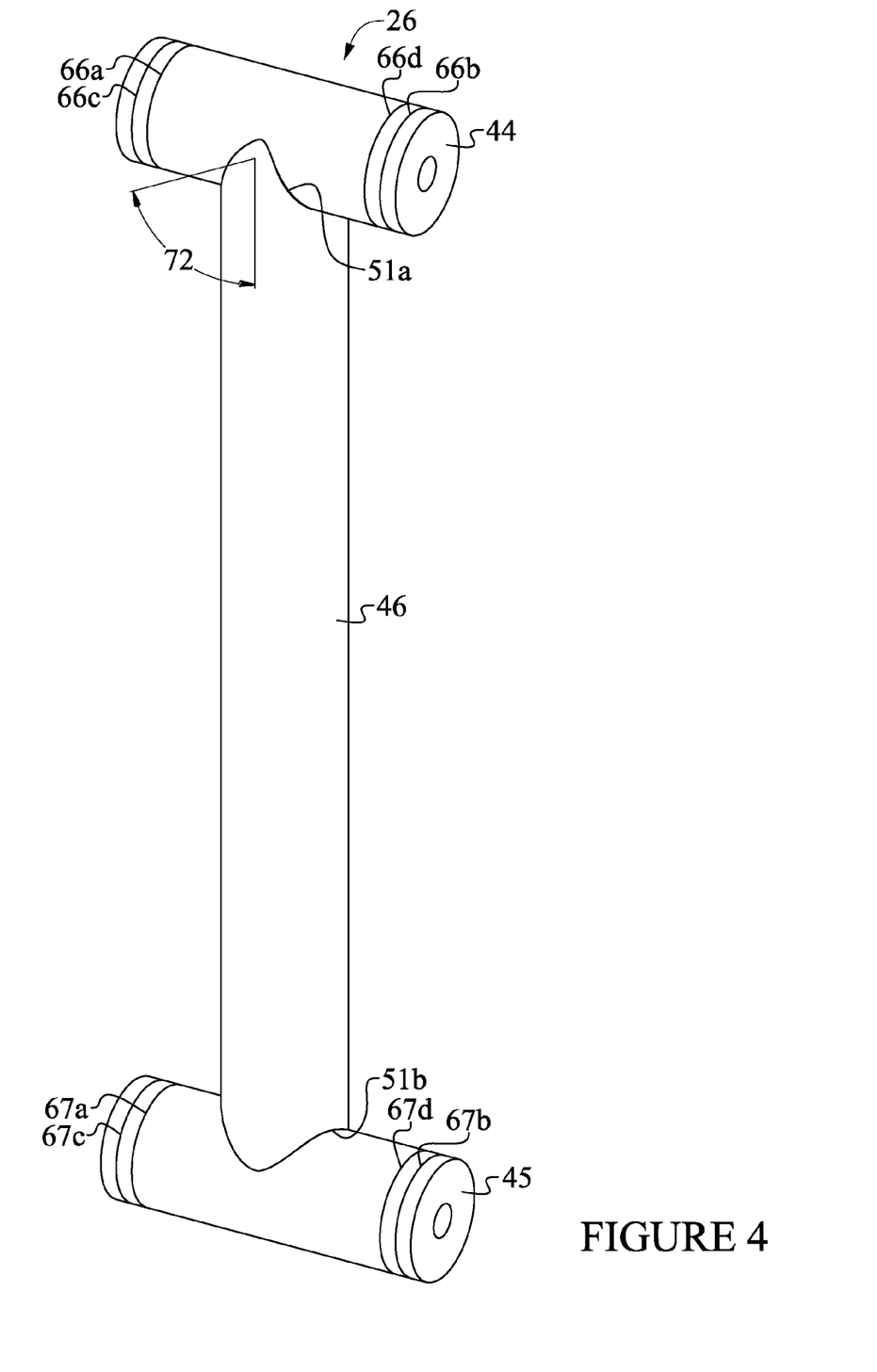
FIG. 4 shows a customizable traction device.

FIG. 4 shows an embodiment of a customizable traction device 26 having a shearable traction head 44, a traction body 46, and a shearable lower back traction 45.

The shearable traction head 44 can have a plurality of dimensional indicators 66*a*, 66*b*, 66*c*, and 66*d*. The shearable lower back traction 45 can have a plurality of dimensional indicators 67*a*, 67*b*, 67*c*, and 67*d*. An angle of engagement 72 between the shearable traction head 44 and the traction body 46 is shown.

An adhesive 51*a* can provide engagement between the shearable traction head 44 and the traction body 46. An adhesive 51*b* can provide engagement between the traction body 46 and the shearable lower back traction 45.

Figure 5A:
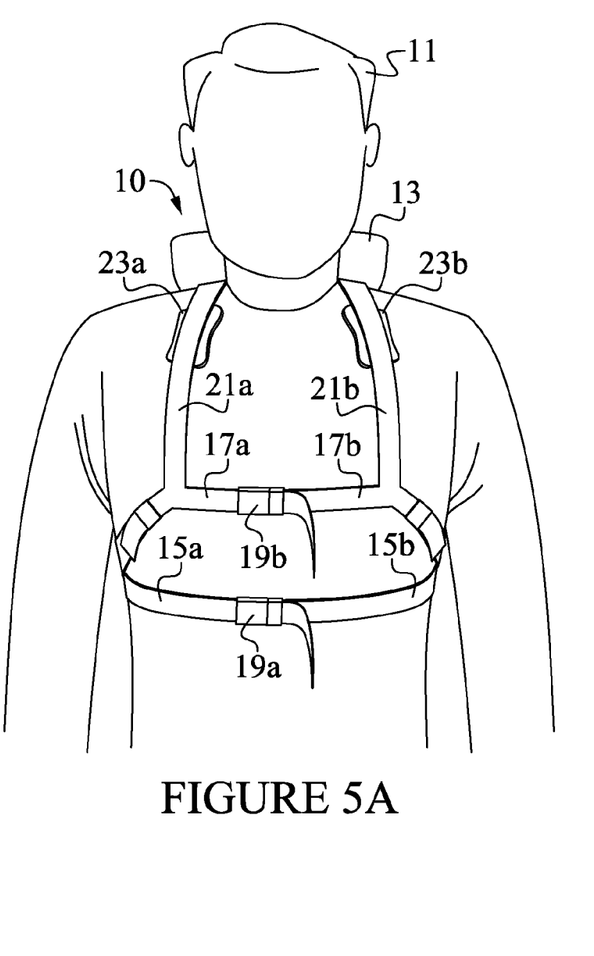
FIG. 5A shows a front view of a user wearing a back and neck cushion therapy device with a harness.

FIG. 5A shows a front view of an embodiment of a back and neck cushion therapy device 10 being worn by a user 11. A pouch 13 can be disposed over the user's back.

The pouch 13 can have a harness with a first adjustable lower webbing strap 15*a* connected to a second adjustable lower webbing strap 15*b* with a buckle 19*a*.

The pouch 13 can have a harness with a first adjustable upper webbing strap 17*a* connected to the first adjustable lower webbing strap 15*a*, and a second adjustable upper webbing strap 17*b* connected to the second adjustable lower webbing strap 15*b*. The first adjustable upper webbing strap 17*a* can be connected to the second adjustable upper webbing strap 17*b* with a buckle 19*b*.

The pouch 13 can have a harness with a first shoulder webbing strap 21*a* connected to the first adjustable upper webbing strap 17*a*, and a second shoulder webbing strap 21*b* connected to the second adjustable upper webbing strap 17*b*. The first shoulder webbing strap 21*a* can include a first shoulder pad 23*a*, and the second shoulder webbing strap 21*b* can include a second shoulder pad 23*b*.

Figure 5B:
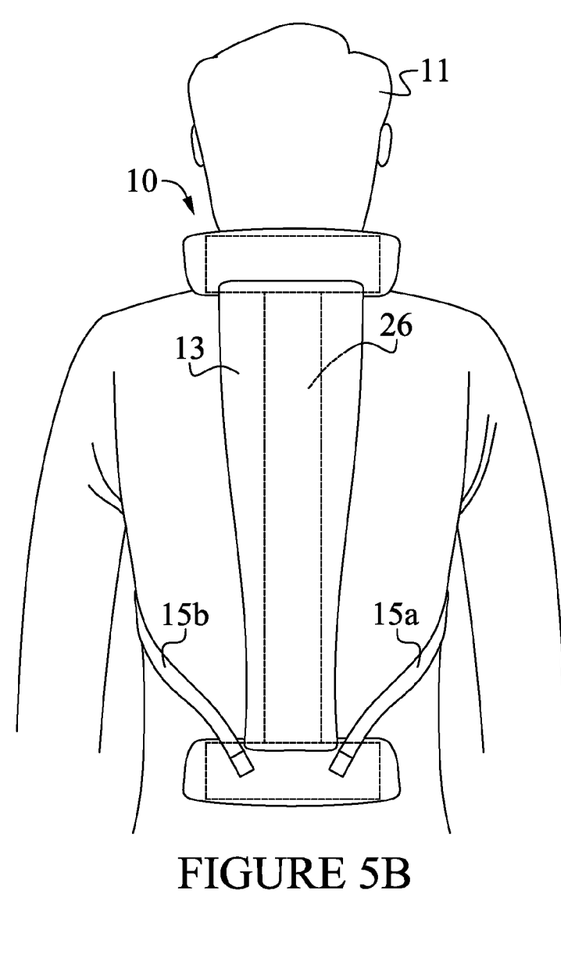
FIG. 5B shows a back view of the user wearing the back and neck cushion therapy device with the harness.

FIG. 5B shows a back view of an embodiment of the back and neck cushion therapy device 10 being worn by the user 11. The pouch 13 can be disposed over the user's back. A traction device 26 can be disposed inside the pouch 13. The first adjustable lower webbing strap 15*a* can be connected to the pouch 13. The second adjustable lower webbing strap 15*b* can also be connected to the pouch 13.

Figure 6:
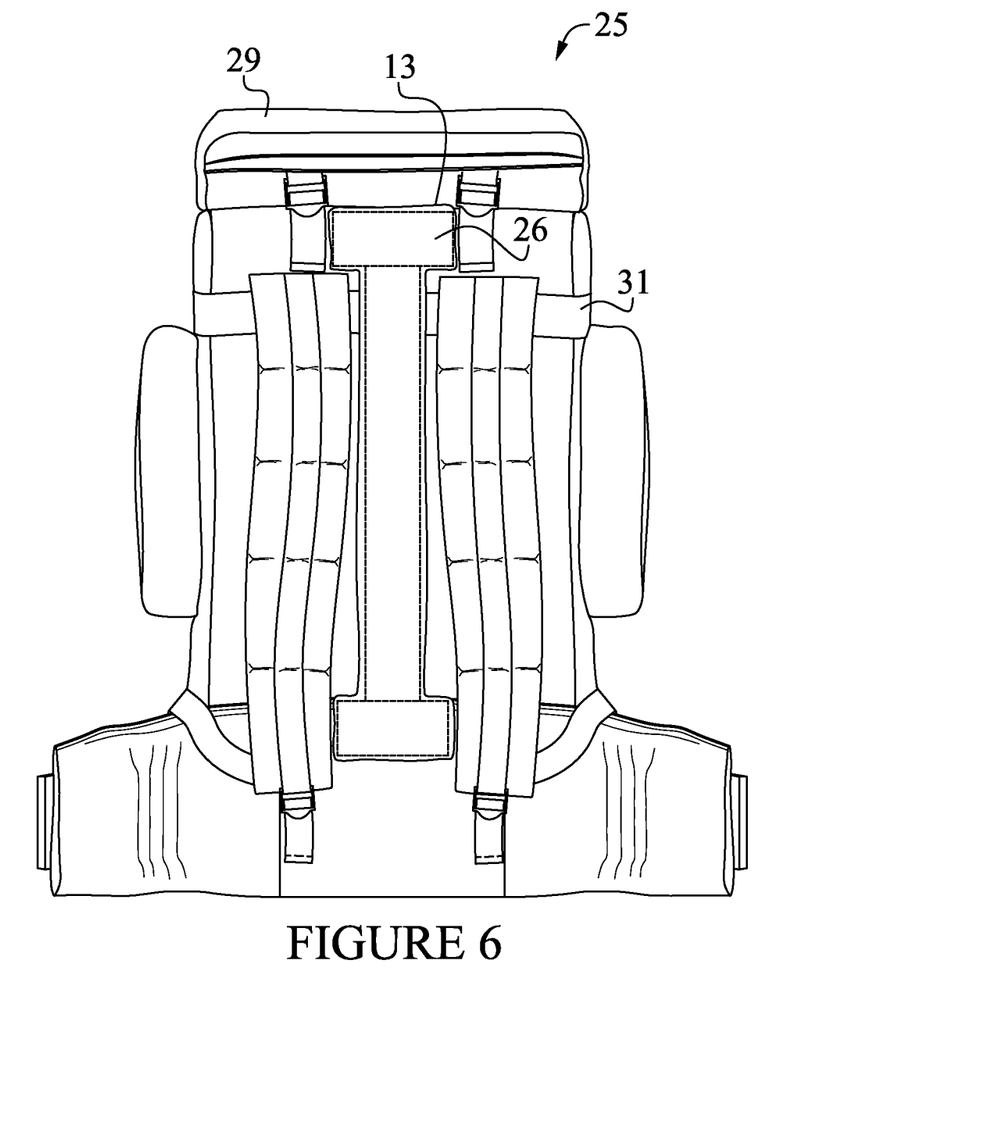
FIG. 6 depicts an embodiment of a backpack with a back and neck cushion therapy device.

FIG. 6 shows an embodiment of a back and neck cushion therapy device 25 with a fabric portion 13 having a traction device 26 disposed therein. The fabric portion 13 can be connected to a backpack 29 with a webbing strap 31. In one or more embodiments, the fabric portion 13 can connect to a frame of a backpack with the webbing strap 31. The fabric portion 13 can conform to a surface of the traction device 26, such that the fabric portion is form fittingly engaged about the surface of the traction device.

Figure 7A:
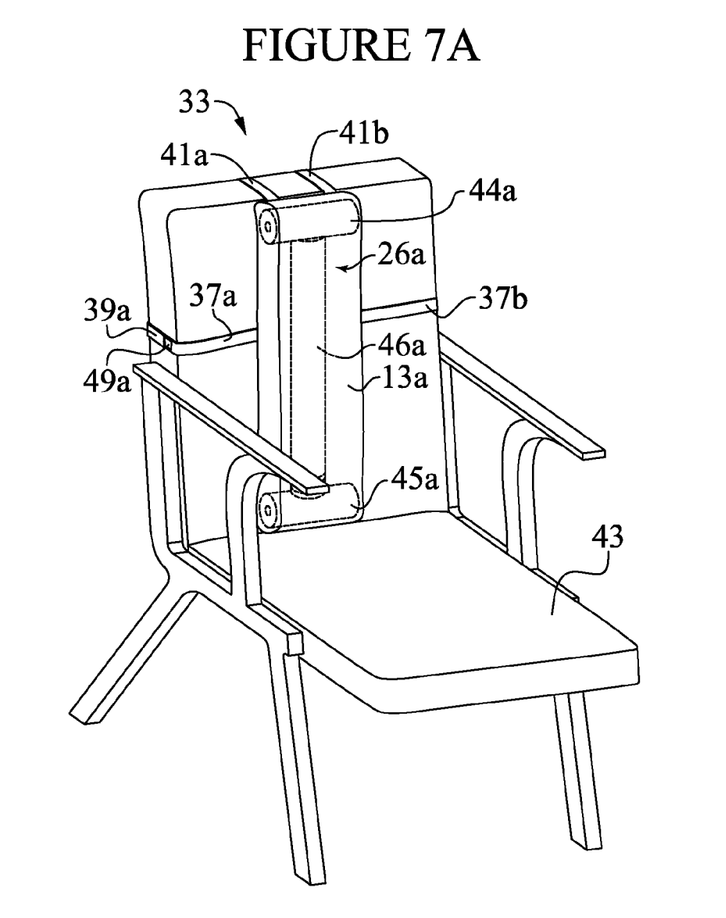
FIG. 7A depicts a front view of an embodiment of a reversible back and neck cushion therapy device.

FIG. 7A shows a front view of an embodiment of a reversible back and neck cushion therapy device 33.

The reversible back and neck cushion therapy device 33 can include a first pouch 13*a* with a first side strap 37*a* and a second side strap 37*b*. The first side strap 37*a* can be connected to a third side strap 39*a*, such as with a hook and loop fastener 49*a*. A first traction device 26*a* can be disposed inside the first pouch 13*a*.

The first traction device 26*a* can include a first traction head 44*a*, a first traction body 46*a*, and a first lower back traction 45*a*.

The reversible back and neck cushion therapy device 33 can hang over a chair 43 with a first connecting strap 41*a* and a second connecting strap 41*b*.

Figure 7B:
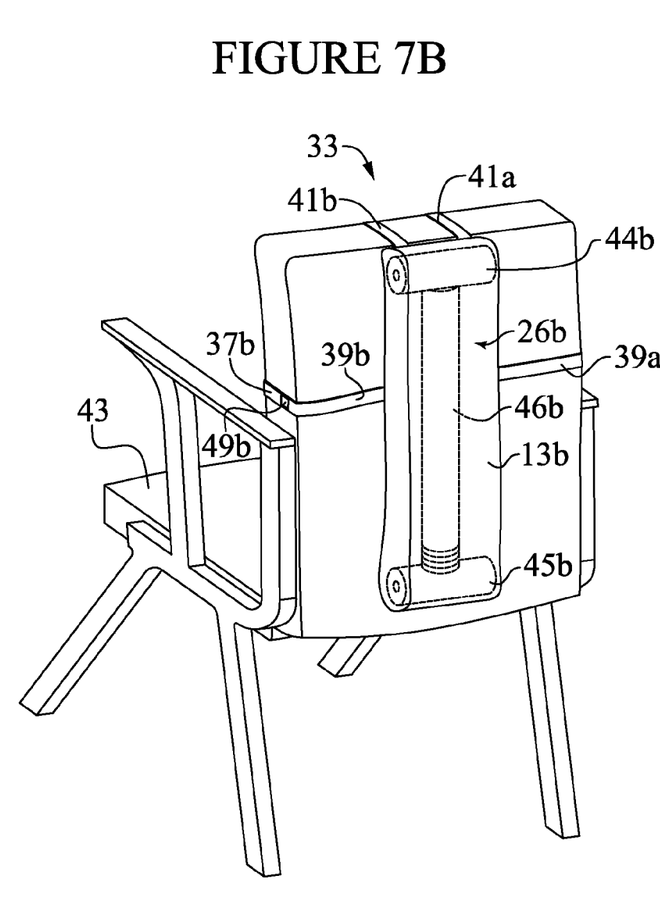
FIG. 7B depicts a back view of the reversible back and neck cushion therapy device.

FIG. 7B shows a rear view of an embodiment of the reversible back and neck cushion therapy device 33.

The reversible back and neck cushion therapy device 33 can include a second pouch 13*b* with the third side strap 39*a*, and a fourth side strap 39*b* connected to the second side strap 37*b*, such as with a hook and loop fastener 49*b*. A second traction device 26*b* can be disposed inside the second pouch 13*b*.

The second traction device 26*b* can include a second traction head 44*b*, a second traction body 46*b*, and a second lower back traction 45*b*.

The first connecting strap 41*a* and the second connecting strap 41*b* can both connect to the second pouch 13*b*, and can provide an engagement between the reversible back and neck cushion therapy device 33 and the chair 43.

While these embodiments have been described with emphasis on the embodiments, it should be understood that within the scope of the appended claims, the embodiments might be practiced other than as specifically described herein.

What is claimed is:

1. A reversible back and neck cushion therapy device comprising:
   a) a first pouch with at least one strap connected thereto;
   b) a first traction device at least partially disposed inside the first pouch, the first traction device comprising: a first traction head connected to a first traction body, wherein the first traction head extends perpendicular to the first traction body;
   c) a second pouch connected to the first pouch with at least one connecting strap, wherein the at least one connecting strap is configured to allow a user to dispose the first pouch and the second pouch over a chair, and wherein the second pouch comprises at least one strap configured to engage the at least one strap of the first pouch;
   d) a second traction device at least partially disposed inside the second pouch, the second traction device comprising: a second traction head connected to a second traction body, wherein the second traction head extends perpendicular to the second traction body, and wherein the second traction device has a lower indention load deflection than the first traction device;
   e) an upper centralizer at least partially located in a first central channel formed in the first traction head and at least partially located in a second central channel formed in the first traction body, wherein the upper centralizer connects the first traction body with the first traction head, wherein the first traction head has a support member disposed therein, wherein the support member comprises a left tube, a right tube, and a central tube, and wherein the upper centralizer is connected with the central tube; and
   f) a lower centralizer extending from a first lower back traction and engaging the first traction body opposite the upper centralizer, providing an engagement between the first traction body and the first lower back traction.

2. The reversible back and neck cushion therapy device of claim 1, wherein the traction devices further comprises a pressure sensor in communication with an alarm, and a time sensor in communication with the alarm, wherein the alarm provides an alert to the user:
   a) when a pressure measured by the pressure sensor is greater than a preset pressure limit;
   b) when a usage time measured by the time sensor is greater than a preset time limit; or
   c) combinations thereof.

3. The reversible back and neck cushion therapy device of claim 1, wherein the first pouch and the second pouch are configured to be simultaneously disposed over a flat rigid surface, allowing the user to receive neck and back stimulation from either the first traction device or the second traction device.

4. The reversible back and neck cushion therapy device of claim 1, wherein:
   g) the first traction device further comprises a first lower back traction connected to the first traction body opposite the first traction head;
   h) the first lower back traction extends perpendicular to the first traction body and parallel to the first traction head;
   i) the second traction device further comprises a second lower back traction connected to the second traction body opposite the second traction head; and
   j) the second lower back traction extends perpendicular to the second traction body and parallel to the second traction head.

5. The reversible back and neck cushion therapy device of claim 4, wherein the first lower back traction is longer than the first traction head, and wherein the second lower back traction is longer than the second traction head.

6. The reversible back and neck cushion therapy device of claim 4, wherein each traction device is shearable, allowing the user to cut each traction device to a custom size.

* * * * *